United States Patent [19]
Drechsler

[11] Patent Number: 5,445,945
[45] Date of Patent: Aug. 29, 1995

[54] METHODS OF REGENERATING METALWORKING FLUIDS WITH CHELATING AGENTS

[75] Inventor: Peter H. Drechsler, New Britain, Conn.

[73] Assignee: The Torrington Company, Torrington, Conn.

[21] Appl. No.: 203,154

[22] Filed: Feb. 28, 1994

[51] Int. Cl.⁶ .......................... B21B 45/02; C12Q 1/02
[52] U.S. Cl. ......................................... 435/29; 72/42; 210/681; 210/764
[58] Field of Search ...................... 435/262, 29; 72/42; 210/656, 681, 749, 764; 252/47.5, 49.5, 56 R; 422/3, 28, 62; 436/55, 60, 73

[56] References Cited

U.S. PATENT DOCUMENTS

| | | | |
|---|---|---|---|
| 4,129,509 | 12/1978 | Shringapurey | 252/49.5 |
| 4,172,140 | 10/1979 | Shull et al. | 424/273 |
| 4,250,046 | 2/1981 | Przybylinski | 252/49.3 |
| 4,294,853 | 10/1981 | Williams et al. | 424/319 |
| 4,307,109 | 12/1981 | Arbir et al. | 424/274 |
| 4,406,812 | 9/1983 | Childers | 252/186.21 |
| 4,828,730 | 5/1989 | Molmans | 252/28 |
| 4,853,131 | 8/1989 | Etani | 210/696 |
| 4,927,550 | 5/1990 | Cutcher | 252/32.5 |
| 5,160,527 | 11/1992 | Law et al. | 71/67 |

FOREIGN PATENT DOCUMENTS 1161026 1/1984 Canada .
1476862 6/1977 United Kingdom .

OTHER PUBLICATIONS

Keith Bienkowski/Waste Minimization Through Improved Coolant Management/1992/pp. 12-1 to 12-6.
Frederick J. Passman/Microbial Problems in Metalworking Fluids/pp. 431-433 J of Soc Tribologists & Lubrication Eng. No Date Avail.
Inger Mattsby-Baltzer et al./Microbial Growth & Accumulation in Industrial Metal-Working Fluids/1989-/vol. 55 No. 10/pp. 2681-2689.
Warren P. Iverson/Mechanism of Anaerobic Corrosion of Steel by Sulfate Reducing Bacteria/Mar. 1984/pp. 28-30.
E. O. Bennett, PhD/Dermatitis in the Metalworking Industry Asle Special Pub SP-11 1983. Lubrication Engineering 1984.
Mohammad Sondossi et al./Factors Affecting Regrowth of Pseudomonas Aeruginosa Following Biocide Treatment/vol. 41, 6, 366-369 1984.
Wilkinson S., Sensitivity to EDTA, pp. 145-188. (AQ) No Date Avail.
Rossmoore H., Biostatic Fluids, Friendly Bacteria . . . J of Soc Tribol & Lub Eng pp. 253-260 1993.

Primary Examiner—William H. Beisner
Assistant Examiner—Ralph Gitomer
Attorney, Agent, or Firm—John C. Bigler

[57] ABSTRACT

Metalworking fluids (MWFs) can be regenerated and stabilized by the controlled addition of a chelating agent. The resulting sequestration of the dissolved metals in the MWF has been found to reduce incidence of dermatitis, to control the growth of microbes including bacteria and fungi, and to reduce the generation of odors, all without the further addition of fresh (virgin) MWF or a conventional biocide.

35 Claims, 4 Drawing Sheets

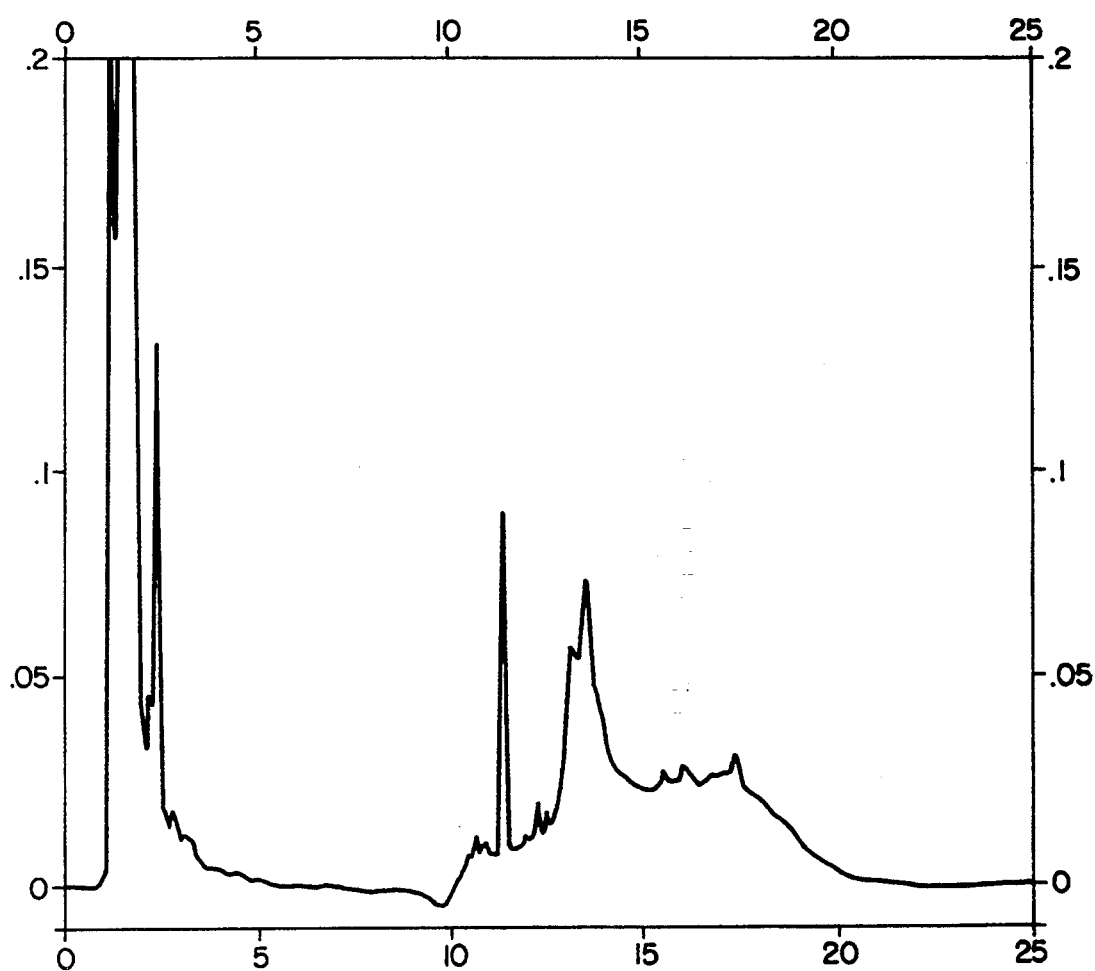
FIG. IA

METHODS OF REGENERATING METALWORKING FLUIDS WITH CHELATING AGENTS

BACKGROUND OF THE INVENTION

The present invention relates generally to metalworking fluids and, more particularly, to methods of using additives to regenerate and stabilize metalworking fluids and to diminish dermatitis and other health problems associated with the use of metalworking fluids. This invention also relates to a wholly or partially automated system for implementing these methods.

In the fabrication of metal parts by machining and by various cold forming processes, a lubricant is often used. In a machining operation that involves cutting or other removal of material from the workpiece, the lubricant aids in removing heat generated by engagement of the cutting tool, in removing chips, turnings, and fines generated during such machining, and in lubricating or protecting newly exposed part surfaces. In cold forming operations, a lubricant may be applied to the slug surface to decrease friction during deformation and to lubricate newly exposed surfaces. For cutting operations, the fluid may be circulated continuously over the workpiece.

Especially for turning and similar lathe operations, the lubricant is typically called a "metalworking fluid." Metalworking fluids (MWFs) are used throughout the manufacturing industry to provide a more efficient material removal or forming operation. Such fluids are selected generally for the purpose of cooling the workpiece and the tool during cutting operations, and to facilitate removal of chips during turning, grinding, and similar operations. MWFs are an important facet of many manufacturing operations in that they provide the required chip and heat removal properties necessary to achieve higher production outputs, increased tool life, and enhanced machined-surface finish and part quality.

MWFs are generally categorized as oil-based, synthetic, or semisynthetic. Oil-based MWFs may be comprised of straight (neat) oils derived from petroleum and/or paraffinic hydrocarbons, natural oils such as vegetable oils, or may be comprised of a synthetic oil such as a siloxane or dibasic ester. Water-based MWFs may comprise a water-soluble oil, a synthetic composition, or a semisynthetic composition. Water-based synthetic fluids are free of mineral oils, and their aqueous environment can spawn bacterial and/or fungal growth. Semisynthetic fluids and water soluble oils generally combine the advantages of emulsifiable oils and synthetic fluids, and they are typically provided as an oil-in-water emulsion. See generally, T. Cole, "Know Your Coolants," *Cutting Tool Eng.*, October 1990, p. 59f.

Conventional additives for MWFs include corrosion inhibitors, such as alkaline and alkanolamine salts of organic acids, sulfonates, amines, amides, organic borate compounds, and others. Corrosion inhibitors are generally added to the hydrophobic portion of the MWF. Polar compounds, such as certain animal or vegetable oils (e.g., castor oil, olive oil, peanut oil), esters of organic acids, and the like are considered to be chemically inactive MWF ingredients. Polar additives function through electrostatic attraction in which the small polar group adsorbs onto the metal surface, and the larger hydrophobic group is solubilized by the oil phase. These characteristics produce a securely anchored monomolecular film (a metallic soap) on the exposed metal surface that functions as a protective barrier.

"Extreme pressure" additives are another type of conventional additive and typically consist of chlorine, phosphorous, or sulfur compounds. These additives may be used in heavy-duty machining operations where the temperature is greater than that tolerated by polar additives, that is greater than about 390° F. (about 200° C.). Other conventional additives include solubilizers (e.g., long-chain alcohols), colorants, fragrances, anti-oxidants, anti-foaming agents, and the like See, e g., Keith Bienkowski, "Waste Minimization Through Improved Coolant Management," Technical Paper No. MRR92-12, Soc. of Mfg. Eng., Dearborn, Mich. (1992).

MWFs are susceptible to microbial attack by bacteria, fungi, and/or yeasts. (collectively termed herein "microbes"), causing one or more symptoms such as odor development, a decrease in pH, a decrease in dissolved oxygen concentration, changes in emulsion stability (for water soluble oils and semisynthetic fluids), increased incidence of dermatitis, workpiece surface-finish blemishes, clogged filters and lines, increased workpiece rejection rates, decreased tool life, and generally unpredictable changes in coolant chemistry. See, e g., Frederick J Passman, "Microbial Problems in Metalworking Fluids," *Lubrication Engineering*, pp. 431-3, May 1988. See also I. Mattsby-Baltzer et al., "Microbial Growth and Accumulation in Industrial Metal-Working Fluids," *Applied and Environmental Microbiology*, October 1989, pp. 2681-2689.

Biocides are typically added to the MWF to combat microbial contamination. One conventional biocide is o-phenylphenol (available as DOWICIDE 1 antimicrobial fluid from Dow Chemical USA, Midland, Mich. Hernandez (Canadian Pat. No. 1,161,026) describes inherently bactericidal MWFs that include a mixture of boric acid, an alkali tetraborate, pelargonic acid (also known as normal ennoic acid or nonanoic acid, $CH_3(CH)_7COOH$), a nonionic surfactant, and water. Biocides typically have a limited lifetime of only a couple or a few days and, accordingly, are replenished weekly if not daily according to conventional manufacturing protocol.

While reported opinions differ as to whether MWFs can transmit communicable disease, and regarding the general viability of microbes in MWFs, it is fairly well-established that used MWFs are associated with outbreaks of dermatitis. Two potential sources of MWF-induced dermatitis are compounds intentionally added to the MWF (such as biocides) and solubilized metal ions from metal chips, dust, and fines, typically collectively referred to as "swarf", deposited in the MWF by the machining or forming operation.

Metal ions can become solubilized in the MWF due to the generation of heat, friction, oxidation, and other chemical and physical processes which occur in the MWF environment. Virtually any metal ion, including iron, nickel, chromium, cobalt, cadmium, copper, manganese, or zinc may cause contact dermatitis in a particular machine operator. Iron, nickel, and chromium are typically found in swarf generated from machining various types of stainless steel. Cobalt is typically encountered when machining with cutting tool steel and tungsten carbide cutting tools.

Bacteria are known to use metal ions in their metabolism. Bacterial metabolism is the typical cause of underarm odor, and so deodorants typically include an antibacterial agent (e.g., benzalkonium chloride, triclosan, etc.). See also Warren P. Iverson, "Mechanism of Anaerobic Corrosion of Steel by Sulfate Reducing Bacteria," *Nat'l Assoc. of Corrosion Eng.*, Paper No. 83-243 (1984). Anaerobic sulfate-reducing bacteria metabolize sulfur-containing compounds present in the MWF introduced from the water source, cutting oil additives, and other contaminants which enter the cooling fluid system. The metabolic product of these sulfur-reducing bacteria is typically hydrogen sulfide, an odious compound.

In spite of the existence of a wide variety of antimicrobial compounds useful for treating MWFs, there are still significant problems associated with microbial growth in MWFs. These problems range from those mentioned above, such as dermatitis and poor workpiece surface finish, to noisome conditions and corrosion of the metalworking machinery. The standard industry practice of recycling MWFs leads to an accumulation of solubilized metals at ever increasing concentrations. See "Dermatitis Is a Key Consideration When Selecting a Coolant," *Lubricants World*, July 1992, p 8. The alternative of frequent replacement of MWFs is costly due to environmental problems associated with disposal.

The foregoing illustrates limitations known to exist in present MWFs and methods. Thus, it is apparent that it would be advantageous to provide an alternative directed to overcoming one or more of the limitations set forth above. Accordingly, a suitable alternative is provided including features more fully disclosed hereinafter.

SUMMARY OF THE INVENTION

In one aspect of the invention, this is accomplished by providing a method for reducing the presence of at least one detrimental microbe in a metalworking fluid (MWF). The method comprises (A) testing a MWF for the presence of microbes and the presence of free metal ions in solution in the fluid, (B) determining the amount or concentration of ions present, and, (C) when the microbes and the metal ions are both present, adding to the metalworking fluid an amount of a chelating agent effective to sequester the metal ions.

In other aspects of the invention methods are provided for regenerating or stabilizing a used MWF, and for reducing the presence of bacteria in a MWF. This invention also provides a system for controlling the state of a recirculating MWF.

The foregoing and other aspects of the invention will become apparent from the following detailed description of the invention when considered in conjunction with the accompanying drawing figures.

BRIEF DESCRIPTION OF THE DRAWING FIGURES

FIGS. 1A, 1B, and 1C depict high performance (high pressure) liquid chromatography (HPLC) analyses of a MWF in a stable environment, in an unstable environment wherein the sample contains microbes, and in an environment that contained microbes but which has been treated according to this invention, respectively;

FIG. 2 depicts a flow diagram of a method for testing and regenerating a MWF according to certain embodiments of this invention; and FIG. 3 depicts an idealized control scheme for controlling a MWF in a circulating sump system.

DETAILED DESCRIPTION

Figure 1B:
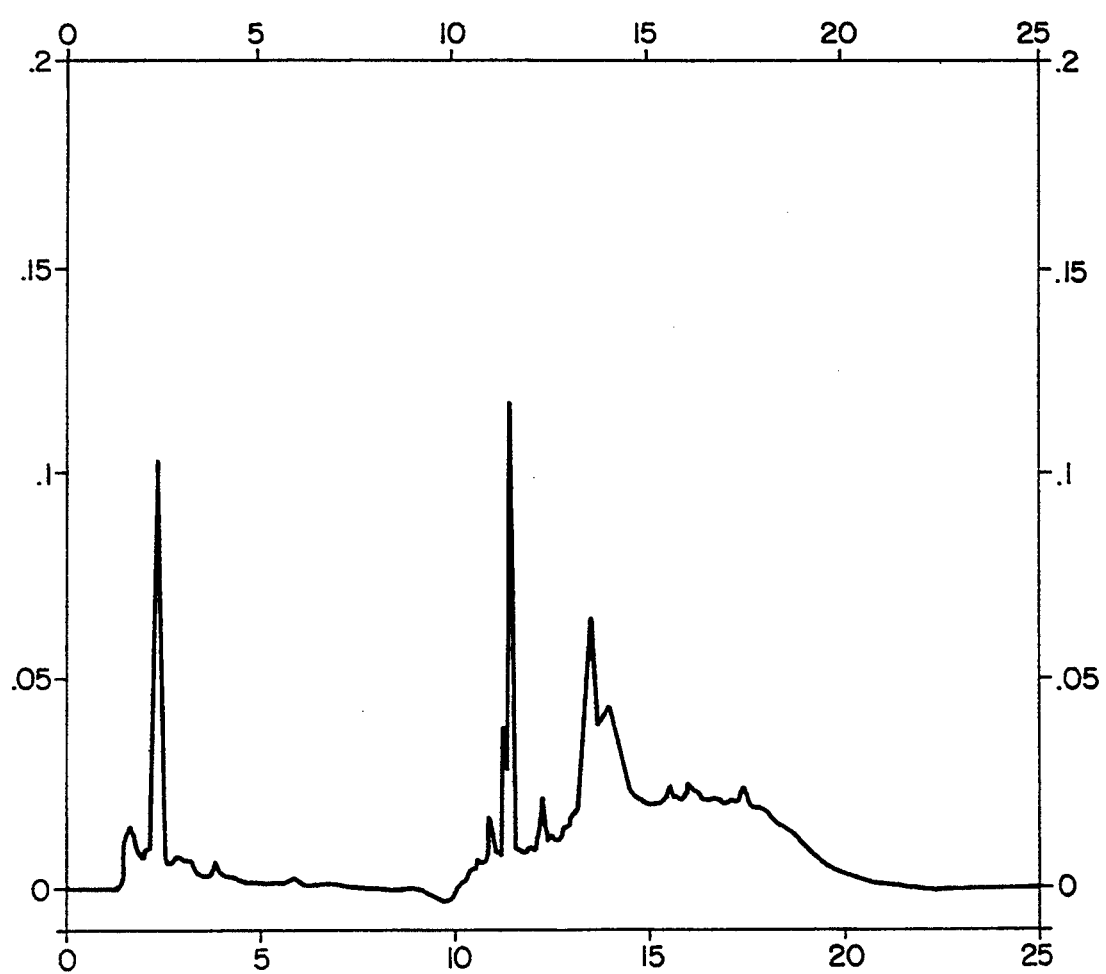

It has been found quite unexpectedly that MWFs can be regenerated and stabilized with the controlled addition of a chelating agent.

While not being constrained to a particular theory, it is believed that metal ions in the MWF contribute directly to contact dermatitis. Further, because certain metal ions are often necessary for the metabolism of certain microbes which generate odors and contribute to dermatitis and other health problems, it is believed a significant number of benefits can be obtained by sequestering the metal ions in a recirculating MWF into inactive forms. Also, it may be that certain bacteria are beneficially present at low concentrations to control yeast and/or fungus populations, whereas higher concentrations of those bacteria have detrimental effects.

The present invention is useful with any recirculating water-based MWF system. Such systems may have a large single reservoir distributing MWF to many machines or a small reservoir supplying a single machine. Small or specialty tooling shops may require the use of several different MWF systems because of the variety of metal compositions machined or the type of operations performed (e.g., turning, grinding, stamping, etc.). The present invention will find general applicability in any environment in which new metal or metal-containing surfaces are created, and such an environment will usually be involved with forming, machining, abrading, and similar operations involving metals, cermets, and ceramics.

Previously, attempts to provide antimicrobial action employed the addition of compounds toxic to the microbes. In contrast, the present invention provides antimicrobial effects by sequestering necessary nutrients from the microbes, essentially using starvation rather than poisoning. The present invention is a more environmentally favorable method, for local flora and fauna as well as for the operator, and for controlling odor, dermatitis, and other microbially-induced problems than is the use of conventional, toxic antimicrobial/biocidal compounds. Chelating agents are typically non-toxic and user-friendly and even when used in amounts greater than required, generally have minimal detrimental effects on the operation of the MWF and the safety of the operator.

There are a number of related occurrences which can cause or exacerbate dermatitis. The composition of the cooling fluid itself may be sufficient. Solubilized metals from the swarf that is carried away in the MWF will be recycled and contact the operator. These metal ions will also foster the growth of bacteria that can cause dermatitis. Other ions may be present in the water supply (typically a municipal water supply), including sulfur-containing compounds, which may themselves cause dermatitis or may act to support the growth of dermatitis-causing microbes.

Metal ions such as iron, chromium, nickel, copper, and the like, which are typically found in alloy workpieces, interact with oxygen, sulfur, and nitrogen ligands. Such ligands are typically found in moieties such as hydroxy, carboxyl, phosphate, carbonyl (keto), thiol, disulfide, amine, and imino. A chelate is a complex formed between a metal (ion) and a compound containing two or more potential ligands (e.g., ethylenediamine). Examples of chelating agents include, without limitation thereto, aminocarboxylic acids such as ethylenediaminetetraacetic acid (EDTA), diethylenetriaminepentaacetic acid (DTPA), triethylenetetraamine hexaacetic acid (TTHA), polyphosphates such as sodium tripolyphosphate and hexametaphosphoric acid, hydroxycarboxylic acids such as tartaric acid, glyoclis acid, and citric acid, deferoxamine (N-(5-(3-((5-amino-pentyl)hydroxycarbamoyl)propionamide)pentyl)-3-((5-N-(hydroxyacetamido)pentyl)carbamoyl)propionhydroxamic acid), acetylacetone such as trifluoroacetylacetone and thenoyltrifluoroacetone, polyamines such as ethylenediamine and triethylenediamine, aminoalcohols such as triethanolamine and diethanolamine, aromatic heterocyclic bases such as dipyridyl and o-phenanthroline, aminophenols such as oxinesulfonicacid and 8-hydroxyquinoline, oximes such as dimethylglyoxime and salicylaldoxime, tetrapyrroles such as tetraphenylporphin and phthalocyanine, sulfur compounds such as dimercaprol (2,3-dimercaptopropanol), penicillamine ($\beta,\beta$-dimethylcysteine), thioglycolic acid and dithiotartaric acid, phenols, and schiff bases, including derivatives and salts thereof, such as disodium EDTA, sodium citrate.

In determining whether regeneration or stabilization of a MWF is required, any one or combination of testing methods can be employed. Cultures for various microbes, including gram-negative and gram-positive bacteria, as well as for yeast and fungi, can be conducted using conventional culturing techniques or using a disposable off-line system such as SANICHECK® BF (available from Bionsan Laboratories, Ferndale, Mich.,), and EASICULT®-TTC (available from Metalworking Chemicals & Equipment Co., Lake Placid, N.Y.). Biological activity can also be estimated by measuring the dissolved oxygen (D.O.) content, assuming that a decreasing amount of D.O. indicates the presence of aerobic bacteria (i.e., a biological oxygen demand, BOD). Various species of Pseudomonas, Legionella, Desulfovibrio, and/or Acinetobacter, as well as Fusarium and/or Candida, may be present in the MWF.

Both aerobic and/or anaerobic bacteria can be present in the MWF system. During operation, when the MWF is being sprayed or otherwise applied to the workpiece and is being pumped around the system, there is typically sufficient agitation of the fluid to entrain air and thereby oxygenate the MWF so that aerobic bacteria can flourish. However, when the system is shut down, for example at the end of each day and over a typical two-day weekend, if not for more extended periods of time, the oil present in the MWF rises and creates a layer of oil floating on the surface of the aqueous-based MWF. This surface oil layer isolates the underlying MWF from the air, such that anaerobic bacteria can flourish in the sump.

In some large systems there are machines which are used infrequently, and the feed lines for the MWF to these machines may be closed but not isolated from the system. Such stagnant pipes ("dead end lines") are a prime place for the growth of microbes. Initiating circulation of MWF in these lines usually results in contamination of the entire system. The microbes in those dead end lines are exposed to a fresh source of dissolved metals and nutrients upon returning to the bulk MWF circulation system. In the present invention, this problem is reduced if not eliminated by sequestering the metal ions these bacteria require for their metabolism.

Often, by the time there is a significant microbial concentration in the MWF, the operation should be shut down to sterilize the system. Accordingly, it is more advantageous to monitor at least one of the parameters such as color, odor, metal ion type and concentration, conductivity, pH, and dissolved oxygen. Inductively coupled argon plasma spectroscopy, atomic absorption spectroscopy, ion chromatography, and other available techniques are suitable for on-line or off-line monitoring of the system. Color is one of the easiest measurement methods and can be done by eye. For example, a conventional synthetic MWF known as CIMCOOL 400 (available from Cincinnati Milacron, Cincinnati, Ohio), originally a clear or translucent bluish or aqua-colored liquid, changes to a distinctly brownish color with use.

A typical used MWF may contain, as a rough estimate, the following amounts of dissolved ions: up to 10 ppm of zinc; up to 200 ppm of iron; up to 0.5 ppm cadmium; up to 1 ppm chromium; and up to 1 ppm copper. An exemplary composition might include 83.36 ppm iron, 4.62 ppm of zinc, 0.08 ppm of cadmium, 0.26 ppm of chromium, and 0.37 ppm of copper. Based on this analysis, an operator would consult the manufacturer's data sheet for a particular chelating agent to determine the amount of chelating agent needed to be added for the effective sequestration of the free metal ions in solution.

For example, Dow Chemical Co. provides literature regarding its VERSENE 100 EDTA product that lists the following parts of chelating agent required to chelate one part of metal: 17.9 parts for iron(II) or iron(III); 8.9 parts for $Cd^{++}$; 15.8 parts for $Cu^{++}$; and 15.3 parts for $Zn^{++}$. No value is given for chromium, but a value of about 17 parts is believed to be fairly accurate. Accordingly, the amount of EDTA (VERSENE 100) needed to sequester the ions of the above exemplary composition would be about 1573.8 ppm. In other words, for a 30,000 gallon system (and assuming the MWF and the EDTA both have the density of water), about 400 pounds should be added. The determination of the amount of chelating agent needed to be effective is thus a function of the particular chelating agent and the types and concentration of dissolved metals freely present in the MWF.

It is within the ability of a person of ordinary skill in this art to determine the amount of a particular chelating agent needed to sequester a particular amount of a particular metal ion. Preferably, manual testing is done on a weekly or biweekly basis to determine the presence of microbes, the biological oxygen demand, the pH, and the like. Given this information, the MWF can be monitored on-line or off-line, a straightforward calculation can be done to determine an effective amount of chelating agent needed to be added, and the addition of chelating agent can then be made automatically or manually.

Various commercially available devices are suitable for automated testing of the condition of the MWF by determining color (e.g., a Model A-2 color analyzer, available from McNab, Inc., Mount Vernon, N.Y.), near-infrared chemical analysis (e.g., a Model KSB analyzer, available from McNab, Inc.), fluorescent analysis (e.g., a Model HSB analyzer, available from McNab, Inc.), light absorption (e.g., a Model AP-VIE analyzer, available from McNab, Inc.), pH (e.g., analyzer Models APII and AP-1H, both available from McNab, Inc.), or UV absorption (e.g., a Model UV-II analyzer, available from McNab, Inc.). The output from such monitoring devices may be directed to a programmable logic controller (PLC) to control a metering device to add an effective amount of the chelating agent.

EXAMPLES

An automated cutting facility having a distributed open MWF system with a capacity of 12,000 gallons was investigated. The materials machined at this facility were composed chiefly of 52100 low-chromium steel alloy. The MWF was FIVE STAR 40b, a semisynthetic grinding fluid available from Cincinnati Milacron (Cincinnati, Ohio). The normal color of this product is a translucent pink color. During normal operations, after a few months, the MWF began exhibiting signs of microbial activity, as noted by the formation of a sulfur dioxide smell (i.e., rotten eggs) and a change in the appearance of the MWF from translucent pink to opaque black.

Samples of the MWF that exhibited these signs of microbial activity were treated with disodium EDTA, trisodium EDTA, and EDTA as follows. Four aliquot portions (10 ml) of the suspect MWF were treated with 300, 600, 900, and 1200 ppm of disodium EDTA; four aliquot portions (10 ml) were treated with 500, 750, 1000, and 1500 ppm of trisodium EDTA; and three aliquot portions (10 ml) were each treated with 2500 ppm of EDTA, disodium EDTA, or trisodium EDTA. As used herein, ppm (parts per million) is on a weight/volume basis, i.e. milligrams per liter; thus, 1000 ppm for a 10 ml sample is about 10 mg of EDTA.

Within two hours of treatment, all samples showed signs of improvement as evidenced by a return of the translucent pink appearance and/or by a diminution in the smell of sulfur dioxide. Within twenty four hours, all of the samples had a more pronounced pink color, with the 2500 ppm EDTA-treated sample showing the greatest improvement. After forty eight hours, all samples having been treated with at least 1000 ppm of EDTA or a salt thereof were entirely pink in appearance; the other samples had varying degrees of pink/black appearances. After seventy two hours, all of the samples had a pink color with no black present by visual inspection, and no sample had an odor of sulfur dioxide. (A control sample to which nothing was added remained black in appearance and retained the sulfur dioxide smell.)

High pressure liquid chromatography analysis of the MWFs revealed that untreated solutions exhibited depletion of MWF components by microbes. That is, a system with a new MWF will reach an equilibrium composition that includes a certain amount of impurities and contaminants, such as oils, dust and fines, and the like. Thereafter, microbial action will consume one or more of the components of the system. Whether the component consumed provides a benefit to the MWF system or is a contaminant, its depletion will throw the system from equilibrium and foster undesired microbial growth. For example, a sulfur-reducing microbe may consume sulfur or a sulfur-containing compound that was introduced intentionally, such as a sulfonate corrosion inhibitor, an extreme pressure additive, or antimicrobial compositions, or by an hydraulic fluid leak, cigarette ashes (or other operator-contributed contaminants typical for an open sump system), and the like.

The MWF in this facility was found to have reductions in the level of dissolved oxygen (D.O.), indicating biological activity. Two months prior to treatment with EDTA, the D.O. averaged 6.82 ppm, one month prior to treatment the D.O. averaged 5.05 ppm, and just prior to treatment the D.O. averaged 2.94 ppm. Based on the preliminary test results, the aforementioned 12,000 gal. system was treated with an amount of EDTA effective to provide a concentration of 500 ppm of EDTA in the MWF (a total of about 50 pounds for 12,000 gal.). After treatment, on the same day, the D.O. level had increased to 8.65 ppm, the average D.O. for the next month was 8.53 ppm, and the average D.O. two months after treatment was 9.96 ppm. A diminution in microbial growth was confirmed by testing for microbes and by the general appearance of the MWF.

Figure 1C:
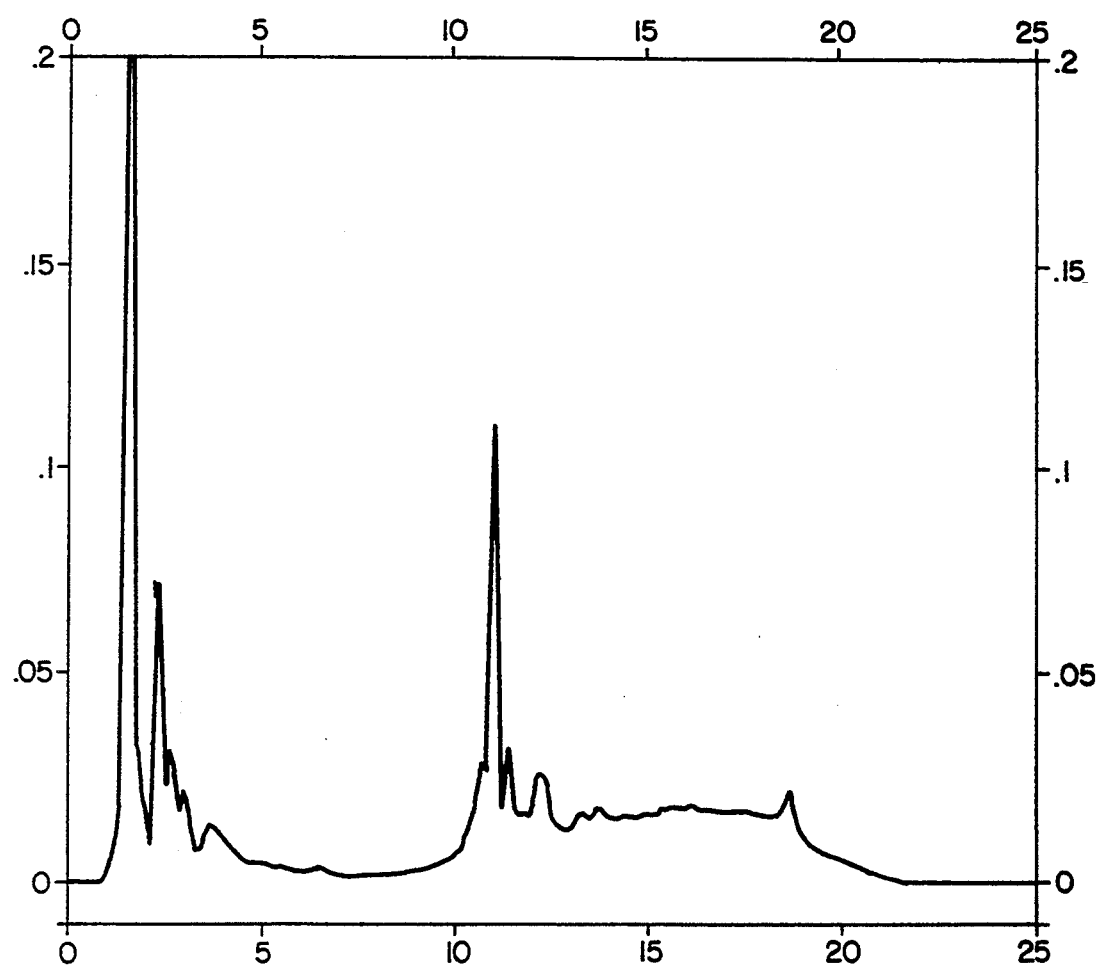

Another example of the functioning of the present invention can be seen with reference to FIGS. 1A, 1B, and 1C, all of which are HPLC analyses of MWFs. FIG. 1A depicts an HPLC analysis of an MWF (containing Five Star 40b) in a stable environment (e.g., no significant microbial growth). (Any given MWF will exhibit a different spectrographic profile because of the presence of other materials and contaminants in the stabilized system.) FIG. 1B depicts the HPCL profile of the same sample after microbial growth has progressed to the point where regeneration or restabilization of the MWF is required. The importance of FIG. 1B is not the presence or absence of particular peaks, but rather that the peaks present in FIG. 1A have diminished due to consumption of the corresponding material by microbial action.

FIG. 1 C is an HPLC graph from a different sample of Five Star 40b that had experienced microbial growth and then had added thereto an effective amount of a chelating agent. From FIG. 1C it can be seen that the MWF has been stabilized to the same general profile as that shown in FIG. 1A by the addition of an effective amount of chelating agent. Again, it is not critically important that the exact same components be present in the MWF after treatment, so long as the MWF is in a stable environment and is protected from being consumed (e.g., a diminution in its components) by microbial action.

Typically, a 12,000 gal. system would require the use of about 100 gal. of biocide annually; at a cost of about $ 300.00/gal., the annual cost for microbial control comes to about $ 30,000.00. The same system was regenerated with about 50 pounds of EDTA; at a cost of about $ 4.00/lb., the expense for regenerating the MWF in this system would be only about $ 200.00. As further described herein, the system should be monitored for the presence of additional free metal ions, which would require subsequent dosing of chelating agent, most likely between 40% and 100% of the initial dose level. Even assuming a total annual addition of about 100 lb., the total annual cost with the present invention ,would be approximately 1% of the typical annual cost using biocides.

Accordingly, by using the present invention, significant economic and environmental advantages can be obtained. MWFs are environmentally hazardous, so when large, central systems need to be recharged, a significant expense is incurred in properly disposing of the used MWF. When a system is recharged, after the used MWF is drained, the system is half filled with new MWF (or water) and soap (or a surfactant and/or detergent) for cleaning. Then the cleaning solution is dumped (and must be disposed of properly) and the system is rinsed with clean MWF (which must also be drained and disposed of properly), and then fresh MWF is added and the system restarted.

A typical large system may contain 30,000 gal. of MWF at a cost of about $ 8.00/gal. for the coolant concentrate (typical dilution of about 20:1; i.e., 1,500 gal. of concentrate for a 30,000 gal. system) and a cost of about 50¢/gal. (diluted basis) for proper disposal of the MWF. The entire amount of the MWF needed for a recharge would be 1,500 gal. concentrate (30,000 gal.) originally dumped, 1,000 gal. concentrate (20,000 gal.) for cleaning, and 1,000 gal. concentrate (20,000 gal.) for rinsing the system, for a total of 3,500 gal. of concentrate, or a cost of $ 28,000.00. The disposal cost for dumping 70,000 gal. (30,000 used MWF dumped plus 20,000 gal. cleaning fluid dumped plus 20,000 gal. rinse fluid dumped) is about $ 35,000.00. Therefore, the total cost can easily be over $ 60,000.00, exclusive of labor costs. On the other hand, a 30,000 gal. system can be regenerated and stabilized with about 175-250 lb. of EDTA annually for a cost of no more than $ 1,000.00 and with less impact on the environment.

It is believed that regular treatment of the MWF according to this invention can extend the working life of the MWF through a number of years, even decades, thereby providing significant economic and environmental advantages over present practices. Thus, by practicing the present invention, new MWF is added only to compensate for losses due to "dragout" (i.e., the MWF remaining on the workpiece when the part is removed), splashing, and the like.

The present invention also provides a method for automating the addition of a chelating agent to achieve decreased dermatitis, decreased microbial growth, and an increased life of the MWF. As mentioned above, various analyses can be performed on-line and/or off-line to provide an indication of the state of the MWF. Once a virgin fluid reaches a dynamic equilibrium, the fluid can be analyzed to determine the amounts and types of metal ions present in solution. From such a determination, an effective amount of chelating agent can be added. After further operation of the system, an analytical method can be used to differentiate between those ions which are free in solution and those ions which have been sequestered by the previous addition of chelating agent.

Ion chromatography is one method for on-line analysis of free metals in solution. Those metal ions which have been previously sequestered are not detected by this method. A suitable ion chromatography measuring apparatus can include a Model 590 pump, a U6K Rheodyne sample injector, an IC-PAK cationic SW column, and a Model 430 conductivity detector (all available from Millipore, Inc., Milford, Mass.). Any other measuring method that can differentiate between chelated ions and free ions (which must be sequestered by the addition of a chelating agent) is suitable for continuous monitoring and future additions of chelating agent to the same MWF.

Figure 2:
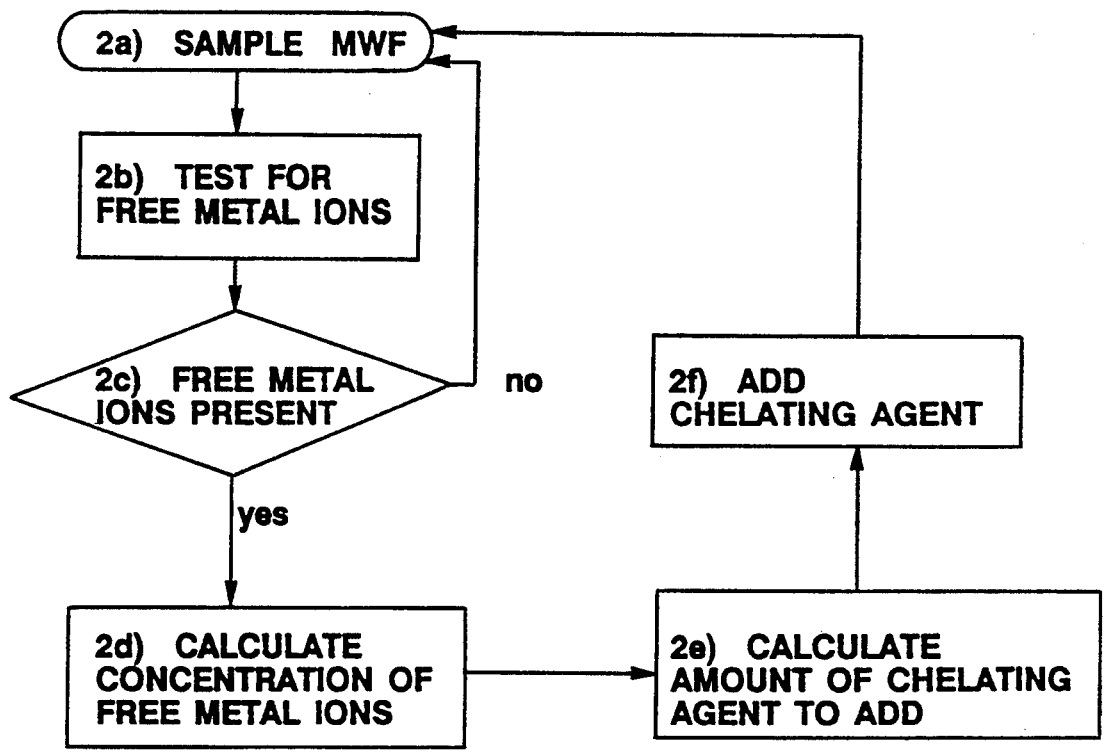

FIG. 2 depicts a flow diagram for practicing the present method. The first step, 2a, involves sampling the MWF for the purpose of testing for the presence of free metal ions (step 2b). If free metal ions are present (step 2c), a calculation is performed to determine the concentration of the free metal ions in the total MWF (step 2d), and then the total amount (generally a weight basis based on the concentration of ions determined and the size of the system) of chelating agent to be added is calculated (step 2e). Finally, chelating agent is added (step 2f) to the MWF in an amount effective to sequester the free metal ions in solution in the MWF.

Figure 3:
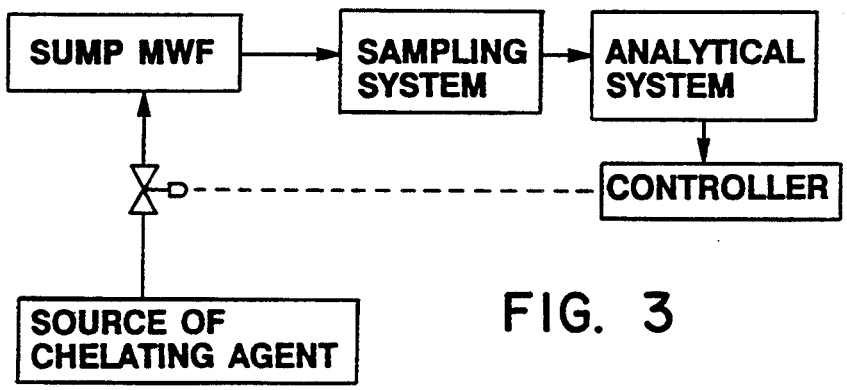

Such a method for controlling the environment of the MWF can be achieved in an automated manner, as shown in FIG. 3. The sump of the system contains the circulating MWF. The MWF is sampled and the sample is analyzed (e.g., by ICAP as described above) to determine the types and concentrations of free metal ions present. A source of chelating agent is provided for addition to the MWF. The result of the analytical system is fed to a programmable logic controller. Shown in simplified form, the controller manipulates a metering mechanism (shown as a valve) to provide the proper amount of chelating agent to the MWF system.

From the above description, it will be apparent that the present invention provides a lowering of microbial counts, thus improving working conditions by providing a reduction in dermatitis and a less odorous environment. By stabilizing and regenerating existing MWFs without having to replace, in whole or in part, the MWF (except for normal losses due to dragout carried away on the machined parts, splashing, etc.), substantial cost savings can be realized while reducing adverse ecological effects.

The foregoing description is meant to illustrate and describe the present invention, and various modifications thereto are intended to be within the scope and spirit of the invention as defined by the following claims.

What is claimed is:

1. A method for reducing the presence of at least one detrimental microbe in a metalworking fluid (MWF), comprising:
    (A) testing a metalworking fluid for the presence of said at least one microbe and the presence of at least one type of free metal ion in solution;
    (B) determining the concentration of said free metal ion in solution in said metalworking fluid; and
    (C) when said at least one microbe and said at least one metal ion are both present, adding to said metalworking fluid an amount of a chelating agent effective to sequester said free metal ion.

2. The method as defined by claim 1, wherein said chelating agent effective to sequester said metal ion is selected from the group consisting of dimercaprol(2,3-dimercaptopropanol), ethylenediamine tetraacetic acid (EDTA), diethylenetriamine pentaacetic acid (DTPA), penicillamine($\beta,\beta$-dimethylcysteine), deferoxamine, triethylenetetraamine hexaacetic acid (TTHA), tetraethylenepentaamine heptaacetic acid (PHA), gluconic acid, salts thereof, derivatives thereof, and mixtures thereof.

3. The method as defined by claim 1, wherein said chelating agent effective to sequester said metal ion is an acetic acid derivative selected from the group consisting of diethylenetriamine pentaacetic acid (DTPA), triethylenetetraamine hexaacetic acid (TTHA), tetraethylenepentaamine heptaacetic acid (PHA), salts thereof, derivatives thereof, and mixtures thereof.

4. The method as defined by claim 1, wherein said metal ion is selected from the group consisting of iron, nickel, chromium, cobalt, cadmium, copper, manganese, zinc, and mixtures thereof.

5. The method as defined by claim 1, wherein said steps (A) and (B) are automated.

6. The method as defined by claim 1, wherein said step (C) is automated.

7. The method as defined by claim 1, wherein said metalworking fluid is a synthetic metalworking fluid.

8. The method as defined by claim 1, wherein said metalworking fluid is a semi-synthetic metalworking fluid.

9. The method as defined by claim 1, wherein said metalworking fluid is a water-soluble oil.

10. The method as defined by claim 1, further comprising, at some time subsequent to said adding of said chelating agent, repeating said steps (A), (B), and (C).

11. A method for reducing the occurrence of dermatitis induced by the composition of a used metalworking fluid, comprising:
(A) testing a used metalworking fluid for the presence of free metal ions in solution;
(B) determining the concentration of said ions in solution in said fluid; and,
(C) adding to said metalworking fluid an amount of a chelating agent effective to sequester said free metal ions and thereby reducing the occurrence of dermatitis induced by the composition of said used metalworking fluid.

12. The method as defined by claim 11, wherein said chelating agent effective to sequester said metal ions is selected from the group consisting of dimercaprol(2,3-dimercaptopropanol), ethylenediamine tetraacetic acid (EDTA), diethylenetriamine pentaacetic acid (DTPA), penicillamine($\beta,\beta$-dimethylcysteine), deferoxamine, triethylenetetraamine hexaacetic acid (TTHA), tetraethylenepentaamine heptaacetic acid (PHA), gluconic acid, salts thereof, derivatives thereof, and mixtures thereof.

13. The method as defined by claim 11, wherein said chelating agent effective to sequester said metal ions is an acetic acid derivative selected from the group consisting of diethylenetriamine pentaacetic acid (DTPA), triethylenetetraamine hexaacetic acid (TTHA), tetraethylenepentaamine heptaacetic acid (PHA), salts thereof, derivatives thereof, and mixtures thereof.

14. The method as defined by claim 11, wherein said metal ions are selected from the group consisting of iron, nickel, chromium, cobalt, cadmium, copper, manganese, zinc, and mixtures thereof.

15. The method as defined by claim 11, wherein said steps (A) and (B) are automated.

16. The method as defined by claim 11, wherein said step (C) is automated.

17. The method as defined by claim 11, wherein said metalworking fluid is a synthetic metalworking fluid.

18. The method as defined by claim 11, wherein said metalworking fluid is a semi-synthetic metalworking fluid.

19. The method as defined by claim 11, wherein said metalworking fluid is a water-soluble oil.

20. The method as defined by claim 11, further comprising, at some time subsequent to said addition of said chelating agent, repeating said steps (A), (B), and (C).

21. A method for regenerating a used metalworking fluid, comprising:
(A) testing a used metalworking fluid for the presence of metal ions;
(B) determining the concentration and types of said ions present; and,
(C) adding to said metalworking fluid an amount of a chelating agent effective to sequester said metal ions and thereby regenerating said used metalworking fluid.

22. The method as defined by claim 21, wherein said metalworking fluid is a synthetic metalworking fluid.

23. The method as defined by claim 21, wherein said metalworking fluid is a semi-synthetic metalworking fluid.

24. The method as defined by claim 21, wherein said metalworking fluid is a water-soluble oil.

25. The method as defined by claim 21, further comprising, at some time subsequent to said addition of said chelating agent, repeating said steps (A), (B), and (C).

26. The method as defined by claim 21, wherein said chelating agent effective to sequester said metal ions is selected from the group consisting of dimercaprol(2,3-dimercaptopropanol), ethylenediamine tetraacetic acid (EDTA), diethylenetriamine pentaacetic acid (DTPA), penicillamine($\beta,\beta$-dimethylcysteine), deferoxamine, triethylenetetraamine hexaacetic acid (TTHA), tetraethylenepentaamine heptaacetic acid (PHA), gluconic acid, salts thereof, derivatives thereof, and mixtures thereof.

27. The method as defined by claim 21, wherein said chelating agent effective to sequester said metal ions is an acetic acid derivative selected from the group consisting of diethylenetriamine pentaacetic acid (DTPA), triethylenetetraamine hexaacetic acid (TTHA), tetraethylenepentaamine heptaacetic acid (PHA), salts thereof, derivatives thereof, and mixtures thereof.

28. The method as defined by claim 21, wherein said metal ions are selected from the group consisting of iron, nickel, chromium, cobalt, cadmium, copper, manganese, zinc, and mixtures thereof.

29. The method as defined by claim 21, wherein said testing and determining steps are automated.

30. The method as defined by claim 21, wherein said adding step is automated.

31. A method for reducing the presence of one or more microbes in a metalworking fluid, which comprises:
(A) determining whether undesirable microbes exist in said metalworking fluid; and,
(B) if such undesirable microbes exist, adding to said metalworking fluid an amount of a chelating agent effective to sequester metal ions which are microbial nutrients therein and thereby reducing the presence of said one or more microbes in said metalworking fluid.

32. The method as defined by claim 31, wherein said undesirable microbes include at least one bacteria selected from the group consisting of those of the genera Pseudomonas, Legionella, Desulfovibrio, and Acinetobacter.

33. The method as defined by claim 31, wherein said undesirable microbes include at least one yeast selected from the group consisting of those of the genera Fusarium, and Candida.

34. The method as defined by claim 31, wherein said chelating agent effective to sequester said metal ions is selected from the group consisting of dimercaprol(2,3-dimercaptopropanol), ethylenediamine tetraacetic acid (EDTA), diethylenetriamine pentaacetic acid (DTPA), penicillamine($\beta,\beta$-dimethylcysteine), deferoxamine, triethylenetetraamine hexaacetic acid (TTHA), tetraethylenepentaamine heptaacetic acid (PHA), gluconic acid, salts thereof, derivatives thereof, and mixtures thereof.

35. The method as defined by claim 31, wherein said chelating agent effective to sequester said metal ions is an acetic acid derivative selected from the group consisting of diethylenetriamine pentaacetic acid (DTPA), triethylenetetraamine hexaacetic acid (TTHA), tetraethylenepentaamine heptaacetic acid (PHA), salts thereof, derivatives thereof, and mixtures thereof.

* * * * *